United States Patent [19]

Belloc et al.

[11] 4,288,556

[45] Sep. 8, 1981

[54] MICROORGANISM AND PROTEOLYTIC ENZYME DERIVED THEREFROM

[75] Inventors: André Belloc, Vanves; Jean Florent, Boulogne sur Seine; Jean Lunel, Paris; Jean-Claude Palla, Thiais; Denise Mancy, Charenton le Pont, all of France

[73] Assignee: Rhone-Poulenc Industries, Paris, France

[21] Appl. No.: 825,055

[22] Filed: Aug. 16, 1977

[30] Foreign Application Priority Data

Aug. 24, 1976 [FR] France .............................. 76 25631

[51] Int. Cl.$^3$ .......................... C14C 1/00; C12N 9/52; C12N 1/20
[52] U.S. Cl. .................................. 435/265; 435/212; 435/219; 435/886; 435/253

[58] Field of Search ...................... 195/6, 65, 66 R, 62; 435/212, 219, 220, 886, 265

[56] References Cited

U.S. PATENT DOCUMENTS

| | | | |
|---|---|---|---|
| 3,875,005 | 4/1975 | Belloc et al. | 195/62 |
| 3,966,551 | 6/1976 | Monsheimer et al. | 195/6 |
| 4,066,503 | 4/1975 | Bashkovich et al. | 195/62 |

*Primary Examiner*—Lionel M. Shapiro
*Attorney, Agent, or Firm*—Burns, Doane, Swecker & Mathis

[57] ABSTRACT

A novel culture of the microorganism *Streptomyces caligosus* DS 14,486 and a novel proteolytic enzyme produced from cultivating the culture are disclosed. The enzyme has utility in the depilation of animal skins.

14 Claims, No Drawings

MICROORGANISM AND PROTEOLYTIC ENZYME DERIVED THEREFROM

BACKGROUND OF THE INVENTION

1. Field of the Invention

The present invention relates to a new proteolytic enzyme designated by the number 24,199 RP, and its use in a process for the depilation of animal skins. The new enzyme is obtained by culture, in artificial media, of a micro-organism belonging to the genus Streptomyces and designated by the name *Streptomyces caligosus* DS 14,486 (NRRL 8,195).

2. Summary of the Invention

It is an object of the present invention to provide a novel culture of the microorganism, *Streptomyces caligosus* DS 14,486 which is capable of providing the proteolytic enzyme designated by the number 24,199 RP, in a recoverable quantity upon culturing in a nutrient medium containing assimilable sources of carbon and nitrogen and inorganic constituents.

Another object of the invention is to provide a process for preparing the proteolytic enzyme designated by the number 24,199 RP from a culture of the microorganism *Streptomyces caligosus* DS 14,486.

Still another object of the invention is to provide an improved process for the depilation of animal skins in tanning operations which comprises contacting the skins with the proteolytic enzyme 24,199 RP prepared from a culture of the microorganism *Streptomyces caligosus* DS 14,486.

Other objects and advantages of the present invention will become apparent to those of skill in the art upon studying the detailed description which follows.

DETAILED DESCRIPTION OF THE INVENTION 24,199 RP is a protein substance which exists in the form of a powder having a brown to black color, which is rather soluble in water, slightly soluble in concentrated aqueous solutions of neutral salts, such as ammonium sulphate, and in aqueous-alcoholic or aqueous-acetone mixtures and virtually insoluble in anhydrous alcohols and ketones. Its molecular weight is about 27,000 and its isoelectric point is about 3.7. The proteolytic activity of enzyme 24,199 RP is exerted on a large number of substrates of protein nature such as casein, hemoglobin, fibrin (lysis of clots) or milk (coagulation).

The activity on casein is determined in accordance with a technique similar to that taught by M. Kunitz, J. Gen. Physiol., 30, 291 (1947). The peptides soluble in trichloroacetic acid which are liberated during the hydrolysis are determined either by spectrophotometry at 280 nm, the activity being expressed in Kunitz units (K.U.), or by colorimetry in accordance with the method of O. H. Lowry et al, J. Biol. Chem. 193, 265 (1961), the activity being expressed in mg of tyrosine formed per minute under the conditions of the determination.

The coagulant activity on milk is determined in accordance with a technique based on that taught by N. J. Berridge, Biochem. J., 39, 179 (1945) and can be expressed in rennet units (R.U.), which are defined as follows: 1 rennet unit is the amount of enzyme which coagulates 10 cm$^3$ of reconstituted milk in 100 seconds.

The fibrinolytic activity is determined on a standard fibrin clot produced by the action of thrombin on fibrinogen and can be expressed in lysis units, which are defined as follows: a solution contains 100 lysis units per cm$^3$ (100 LU/cm$^3$) if it causes the lysis of a standard fibrin clot in 30 minutes.

Table I summarizes the results obtained on different substrates with enzyme 24,199 RP according to the present invention. The purified enzyme gave the results shown in the table below:

TABLE I

| SUBSTRATE | REACTION | ACTIVITY |
|---|---|---|
| casein | proteolysis (a) | 1,470 KU/g |
| milk | coagulation (b) | 14,500 RU/g |
| fibrinogen | lysis of a fibrin clot (c) | 4,920 LU/mg |

(a) reaction at pH 7.5 and at 37° C. - concentration in the substrate 5 g/l
(b) reaction at pH 6.35 and at 32° C. - on reconstituted milk
(c) reaction at pH 7.5 and at 37° C.

Table II summarizes the results obtained during the hydrolysis of the casein as a function of the pH.

TABLE II

| pH of the reaction medium | Proteolytic activity on casein at 37° C.: mg of tyrosine formed per g of enzyme |
|---|---|
| 3.5 | 220 |
| 4.0 | 410 |
| 4.5 | 900 |
| 5.0 | 1,370 |
| 5.5 | 1,540 |
| 6.0 | 1,510 |
| 6.5 | 1,930 |
| 7.0 | 2,140 |
| 7.5 | 2,270 |
| 8.0 | 2,180 |
| 8.5 | 1,990 |
| 9.0 | 660 |

The specificity of the enzyme towards the keratins of skins and leathers, glycoproteins, hair roots, and animal skins cannot be deduced from the activities observed on the conventional substrates shown below, but can only be determined by actual depilation experiments such as those described in Examples 4 and 5, infra.

The activity of enzyme 24,199 RP manifests itself over a wide range of pH. Although the optimum value of the pH for hydrolysis of the casein is about 7.5, the enzyme retains at least about 60% of its maximum activity within the pH range between about 5 and 8.5.

Table III summarizes the results obtained on hydrolysis of casein as a function of the temperature.

TABLE III

| Temperature of the reaction medium in °C. | Proteolytic activity on casein at pH 7.5: mg of tyrosine formed per g of enzyme |
|---|---|
| 25 | 1,360 |
| 30 | 1,740 |
| 40 | 2,230 |
| 45 | 2,250 |
| 50 | 1,770 |
| 55 | 680 |
| 60 | 200 |

The optimum activity of enzyme 24,199 RP occurs at a temperature of about 45° C. and the activity decreases rapidly when the temperature is above about 50° C.

Table IV summarizes the results relating to the kinetics of the hydrolysis of casein by enzyme 24,199 RP at a concentration of 10 μg/cm$^3$. The activity is expressed in mg of tyrosine formed.

TABLE IV

| Hydrolysis time in minutes | mg of tyrosine in the reaction medium |
| --- | --- |
| 5 | 0.100 |
| 15 | 0.300 |
| 20 | 0.370 |
| 30 | 0.380 |
| 60 | 0.850 |
| 90 | 1.130 |

The organism which produces the proteolytic enzyme 24,199 RP is a strain of Streptomyces which was isolated from a sample of soil and given the number designation DS 14,486. A sample of this strain has been deposited with the Northern Regional Research Laboratory of the U.S. Department of Agriculture at Peoria, Ill. (United States of America) where it has been registered under number NRRL 8,195. A sample of this strain will be issued freely to any one on reference to the present document.

The microorganism which is the subject of the present invention exhibits characteristics which are not typical of any known species and so must be considered a new species. Accordingly, it has been designated by the name *Streptomyces caligosus,* DS 14,486. It was isolated following the general method which comprises suspending a small amount of soil in sterile distilled water, diluting the suspension to various concentrations and spreading a small volume of each dilution on the surface of Petri dishes containing a nutrient agar medium. After an incubation of several days at 26° C., which allows the microorganisms to develop, the colonies are removed and transferred onto nutrient agars in order to obtain more copious cultures thereof.

*Streptomyces caligosus* DS 14,486 forms cylindrical spores measuring about 0.8 to 1.0μ by 0.6 to 0.8μ. It exhibits sporophores in clusters. The chains of spores are generally rather long, numbering up to several tens of spores, and coil up in tight more or less elongated spirals, usually forming 2 to 3 turns and quite frequently up to six or eight and often even ten turns. Based upon its mode of sporulation, *Streptomyces caligosus* DS 14,486 falls within the Spira section of the Pridham classification.

*Streptomyces caligosus* DS 14,486 develops well at about 26° C., poorly at about 37° C. and fails to develop at about 50° C. It exhibits a sporulated aerial mycelium of grey color. The coloration of its vegetative mycelium ranges, depending on the culture media, from more or less deep brown to black-brown. On organic media, particularly the Waksman special tyrosine-yeast extract agar ("melanin formation medium") it generally exhibits a rather copious production of melanin pigment which imparts a dark tint to the medium. On other synthetic media it produces a blackish soluble pigment in varying quantities.

In cultures at 26° C., it exhibits the following biochemical characteristics:

| | |
| --- | --- |
| production of melanin | positive |
| production of H$_2$S | positive |
| tyrosinase | positive |
| liquefaction of gelatin | positive |
| utilization of cellulose | positive |
| production of nitrites from nitrates | zero on nitrate-containing nutrient broth, positive on synthetic media |
| hydrolysis of starch | positive |
| culture on skimmed milk | peptonization without coagulation |

The cultural characteristics of *Streptomyces caligosus* DS 14,486 are summarized in Table V. They are the characteristics of cultures which have reached a good stage of development, that is to say after about 3 weeks at 26° C., unless otherwise indicated. These characteristics were observed on nutrient agars and broths regularly employed for determining the morphological characteristics of Streptomyces strains, the cultures on agar media being carried out on slant agars. A certain number of the culture media employed were prepared in accordance with the formulations indicated in "The Actinomycetes", S. A. Waksman, pp. 193-197, Chronica Botanica Company, Waltham, Mass., U.S.A., 1950. These cases are indicated by the letter W followed by the number which has been given to them in "The Actinomycetes". The references or compositions of the other culture media are as follows:

Ref. A: "Hickey and Tresner's Agar"—T. G. Pridham et al—Antibiotics Annual, 1956-1957, p. 950.

Ref. B: "Bennett's Agar"—S. A. Waksman—The Actinomycetes vol. 2, p. 331, No. 30; The William and Wilkins Company, Baltimore 1961.

Ref. C: Formula W-23, with the addition of 2% of sugar.

Ref. D: "Yeast Extract Agar"—T. G. Pridham et al—Antibiotics Annual, 1956-1957, p. 950.

Ref. E: "Tomato Paste Oatmeal Agar"—T. G. Pridham et al—Antibiotics Annual, 1956-1957, p. 950.

Ref. F: "Melanin formation medium"—The Actinomycetes, vol. 2, p. 333, No. 42—S. A. Waksman—The Williams and Wilkins Company, Baltimore, 1961.

Ref. G: W. E. Grundy et al—Antibiotics and Chem. 2, 401, 1952.

Ref. H: "Inorganic Salts—Starch Agar"—T. G. Pridham et al—Antibiotics Annual, 1956-1957, p. 951.

Ref. I: corresponds to formula W-1, with 3% of sucrose replaced by 1.5% of glucose.

Ref. J: corresponds to formula W-1, with 3% of sucrose replaced by 1.5% of glycerol.

Ref. K: corresponds to formula W-18, with 3% of sucrose replaced by 1.5% of glucose.

Ref. L: corresponds to formula W-18, with the sucrose omitted and replaced by small strips of filter paper partially immersed in the liquid.

Ref. M: "Manual of Methods for Pure Culture Study of Bacteria: of the Society of American Bacteriologists, Geneva, N.Y., II 50-18.

Ref. N: "Plain Gelatin"—prepared in accordance with the instructions in the "Manual of Methods for Pure Culture Study of Bacteria" of the Society of American Bacteriologists, Geneva, N.Y., II 50-18.

Ref. P: skimmed milk in the form of a commercially available powder, reconstituted in accordance with the manufacturer's instructions.

Ref. Q: medium given for investigation of the production of H$_2$S, by: H. D. Tresner and F. Danga—Journal of Bacteriology, 76, 239-244, 1958.

TABLE V

| Culture medium | Degree of Development | Vegetative mycelium or underside of the culture | Aerial apparatus (comprising the combination of the aerial mycelium and of the sporulation) | Soluble pigment | Observations and biochemical properties |
|---|---|---|---|---|---|
| Hickey and Tresner agar (REF. A) | Good | Underside black brown | Greyish white to grey, well developed | Black brown | Cylindrical spores, measuring 0.8 to 1.04μ, by 0.6 to 0.8, sporophores in clusters, chains of long spores coiling up in tight more or less elongated spirals |
| Bennett agar (Ref. B) | Good | Underside deep yellow brown | Grey, rather well developed | Very deep brown grey | |
| Emerson agar (Ref. C) | Rather good | Vegetative mycelium deep yellow brown | Whitish, in the form of traces | Blackish brown | |
| Pridham yeast extract agar (Ref. D) | Very good | Underside black brown | Deep grey, very well developed | Black | |
| Pridham oatmeal and tomato extract agar (Ref. E) | Very good | Underside black | Deep, grey, very well developed | Black | |
| Peptone glucose agar (W-7) | Good | Vegetative mycelium deep greyish brown | Greyish white, very moderately developed | Black Brown | |
| Nutrient agar (W-5) | Moderate | Vegetative mycelium blackish | Greyish, very poorly developed | Black | Production of melanin: positive (readings carried out in accordance with the recommendations of the author) |
| Krainsky calcium malate agar (Ref. G) | Very moderate | Vegetative mycelium light brownish grey | None | Weak brownish grey | Solubilisation malate: positive |
| Ovalbumin agar (W-12) | Very moderate | Underside brownish grey | Grey, very poorly developed | Blackish grey | |
| Glucose-asparagin agar (W-2) | Good | Underside black | Greyish white to grey, well developed | Blackish grey | |
| Glycerol-asparagin agar (W-3) | Good | Underside black | Greyish black to grey, rather well developed | Blackish grey | |
| Pridham starch-mineral salts agar (Ref. H) | Rather good | Underside deep brown to blackish | Whitish to grey, average development | Deep brown grey | Cylindrical spores, measuring 0.8 to 1.0μ by 0.6 to 0.8μ. Sporophores in clusters, long chains of spores coiling up in tight more or less elongated sprirals. Hydroylsis of starch: positive |
| Starch-nitrate agas (W-10) | Average | Underside light yellow brown | Whitish to grey, moderately developed | Weak Brownish | Hydrolysis of starch: positive |
| Czapek synthetic agar with sucrose (W-1) | Good | Vegetative mycelium greyish to brownish, underside yellow brown | Whitish, in the form of traces | Weak greyish brown | |
| Czapek synthetic agar with glucose (Ref. I) | Rather good | Vegetative mycelium yellow brown, underside yellow brown | Whitish, in the form of traces | Light brownish | |
| Czapek synthetic agar with glycerol (Ref. J) | Rather good | Vegetative mycelium yellow brown to blackish grey brown, underside yellow brown to blackish brown | Greyish white in the form of traces | Greyish brown | |
| Starch-nitrate broth (W-19) | Rather good | Thick velum, underside light brownish | Greyish white, moderately developed | None | Production of nitrites: positive |
| Czapek | Moderate | Flocculent culture | None | None | Production of |

TABLE V-continued

| Culture medium | Degree of Development | Vegetative mycelium or underside of the culture | Aerial apparatus (comprising the combination of the aerial mycelium and of the sporulation) | Soluble pigment | Observations and biochemical properties |
|---|---|---|---|---|---|
| glucose broth (Ref. K) | | and greyish white velum | | | nitrites: positive |
| Czapek cellulose broth (Ref. L) | Moderate | Flocculent culture greyish white | Greyish, moderately developed on the paper protruding from the broth | None | Utilization of cellulose: positive. Production of nitrites: positive |
| Nitrate nutrient broth (Ref. M) | Moderate | Brownish ring | Whitish, in the form of traces | Very deep brown | Production of nitrites: negative |
| Culture on potato (W-27) | Good | Vegetative mycelium thick and wrinkled, very deep brown | Greyish white to light grey. Rather well developed | Black | Black soluble pigment beginning to diffuse into the potato after 24 hours incubation |
| 12% strength pure gelatin (Ref. N) | Good | Culture well developed at the surface, vegetative mycelium deep brown | None | Deep brown | Liquefaction of gelatine: positive |
| Skimmed milk (Ref. P) | Moderate | Brownish grey ring | None | Very deep brown | Peptonization without coagulation - little variation in the pH, which changes from 6.3 to 6.5 in one month. |
| Tresner and Danga agar (Ref. Q) | Moderate | Vegetative mycelium black brown | None | Black | Production of H$_2$S: positive (readings taken in accordance with the recommendations of the authors) |

Streptomyces caligosus DS 14,486 exhibits a combination of characteristics which does not coincide exactly with any of those strains previously described, and it is for this reason that it must be considered a new species.

Among the species described in Bergey's Manual of Determinative Bacteriology (7th edition, The Williams and Wilkins Company, Baltimore, 1957), as well as in "The Actinomycetes" (vol. 2, S. A. Waksman, The Williams and Wilkins Company, Baltimore, 1961), the species which Streptomyces caligosus DS 14,486 is most similar to is Streptomyces noboritoensis which like the microorganism of the present invention produces melanin pigments on organic media, develops a more or less deep brown to black vegetative mycelium on the majority of its culture media, particularly potato on which it forms a very deep brown vegetative mycelium, and exhibits a sporulated aerial mycelium of grey color. However, Streptomyces noboritoensis differs from the new species in that it does not form regularly coiled chains of spores, does not liquefy gelatin (or does so only slightly) does not give a soluble pigment (or only gives a weak brownish soluble pigment on asparagine glucose agar) and produces a deep red brown soluble pigment on nutrient agar. On the other hand, Streptomyces caligosus DS 14,486 forms chains of spores which coil up in a regular manner to form tight spirals, liquefies gelatin, gives a black soluble pigment on asparagine glucose agar and gives a greyish brown soluble pigment on nutrient agar. Moreover, Streptomyces noboritoensis forms a colorless vegetative mycelium on synthetic agar containing nitrate and sucrose while Streptomyces caligosus DS 14,486 forms a thick, greyish to brownish vegetative mycelium on the same medium. Streptomyces noboritoensis also does not utilize rhamnose or sucrose and utilize arabinose, inositol and xylose only slightly, while Streptomyces caligosus DS 14,486 uses all these sources of carbon profusely.

The ability of Streptomyces caligosus DS 14,486 to utilize various sources of carbon or nitrogen to ensure its development was determined in accordance with the principle of the method of Pridham and Gottlieb (J. of Bact. 56, 107–114, 1948). The degree of development was observed on the base indicated by the authors, replacing either the glucose by the various sources of carbon which were tested, or (NH$_4$)$_2$SO$_4$ by the various sources of nitrogen which were tested.

The results are indicated in Table VI:

TABLE VI

| Sources of carbon tested | Utilization | Sources of nitrogen tested | Utilization |
|---|---|---|---|
| D Ribose | positive | NaNO$_3$ | positive |
| D - Xylose | positive | NaNO$_2$ | positive |
| L - Arabinose | positive | (NH$_4$)$_2$SO$_4$ | positive |
| L - Rhamnose | positive | (NH$_4$)$_2$HPO$_4$ | positive |
| D - Glucose | positive | Adenine | positive |
| D - Galactose | positive | Adenosine | positive |
| D - Fructose | positive | Uracil | positive but slow |
| D - Mannose | positive | Urea | positive |
| L - Sorbose | negative | L - Asparagine | positive |
| Lactose | positive | Glucosamine | positive |
| Maltose | positive | Glycine | positive |
| Sucrose | positive | Sarcosine | positive |
| Trehalose | positive | DL - Alanine | positive |
| Cellobiose | positive | DL - Valine | positive |
| Raffinose | positive | DL - Aspartic acid | positive |
| Dextrin | positive | L - Glutamic acid | positive |
| Inulin | positive | L - Arginine | positive |
| Starch | positive | L - Lysine | positive |

TABLE VI-continued

| Sources of carbon tested | Utilization | Sources of nitrogen tested | Utilization |
| --- | --- | --- | --- |
| Glycogen | positive | DL - Serine | positive |
| Glycerol | positive | DL - Threonine | positive |
| Erythritol | negative | DL - Methionine | positive |
| Adonitol | negative | Taurine | negative |
| Dulcitol | negative | DL - Phenylalanine | positive |
| D - Mannitol | positive | L - Tyrosine | positive |
| D - Sorbitol | positive | DL - Proline | positive |
| Inositol | positive | L - Histidine | positive |
| Salicin | limited | L - Tryptophane Betain | positive |

The process for the preparation of enzyme 24,199 RP comprises culturing *Streptomyces caligosus* DS 14,486 on a suitable medium under suitable conditions and thereafter isolating the product formed during the culture.

The culture of *Streptomyces caligosus* DS 14,486 can be accomplished by any aerobic culture method, as for example, a surface culture or submersed culture, but the latter is to be preferred for reasons of convenience. For this purpose, the techniques of inoculation and fermentation, and the various types of apparatus, which are conventionally employed in the fermentation industry are utilized.

The fermentation medium must contain assimilable sources of carbon and nitrogen, inorganic constituents and, when required, growth factors. All of these constituents can be introduced in the form of well-defined products or as complex mixtures as encountered in biological products of various origins.

As sources of assimilable carbon it is possible to use carbohydrates such as glucose, sucrose, maltose, dextrains, starch or other carbon-containing substances such as sugar alcohols (glycerol) or certain organic acids (lactic acid or citric acid). Certain animal or vegetable oils such as lard oil or soya oil can advantageously supplement or replace these various carbon sources.

The suitable sources of assimilable nitrogen are extremely varied. They can be very simple chemical substances such as inorganic or organic ammonium salts, urea and certain aminoacids. They can also be introduced through complex substances which principally contain nitrogen in a protein form, namely casein, lactalbumin, gluten and their hydrolysis products, soya flour, groundnut meal, fishmeal, meat extract, yeast extract, distiller's solubles and corn-steep.

The inorganic constituents which may be added also vary greatly. Some have a buffering or neutralizing effect, such as the alkali metal and alkaline earth metal phosphates or calcium and magnesium carbonate. Others provide the ionic equilibrium necessary for the development of *Streptomyces caligosus* DS 14,486 and for the propagation of the enzyme 24,199 RP. These include chlorides and sulphates of alkali metals and alkaline earth metals. Finally, some act as activators of the metabolic reactions of *Streptomyces caligosus* DS 14,486. Exemplary of these compounds are the salts of zinc, cobalt, iron, copper and manganese.

The growth factors are products of a vitamin nature such as riboflavin, folic acid and pantothenic acid.

The pH of the fermentation medium at the start of the culture must be between about 5.8 and 7.8 and preferably between about 6.2 and 7.9. The optimum temperature for the fermentation is between about 25° and 30° C. but satisfactory production is achieved at temperatures between about 23° and 33° C. The aeration of the fermentation can vary between rather wide values. However, aerations of 0.3 to 3 liters of air per liter of broth per minute are preferred. The maximum yield of enzyme 24,199 RP is obtained after 2 to 8 days' culture, with the precise time depending on the medium used.

Enzyme 24,199 RP is isolated from the fermentation musts in the following sequential manner: Firstly, the fermentation must is filtered, if need be in the presence of a filtration agent, at a pH which is normally that of the medium at the end of the production phase. Secondly, the resulting filtrate is concentrated to a volume of about 1/5 of the initial volume and enzyme 24,199 RP is precipitated by adding a poor solvent such as acetone. The crude product can be purified by fractional precipitation using inorganic salts, such as ammonium sulphate, in the form of solids or concentrated aqueous solutions, and/or by means of poor solvents for enzyme 24,199 RP, such as acetone. Alternatively, the product can be purified by dialysis across a membrane, preferably a regenerated cellulose membrane.

Enzyme 24,199 RP is particularly useful in the tanning industry where it exhibits utility for the depilation of animal skins in preparing leathers. In this particular application, enzyme 24,199 RP can be used in pure form, although equivalent results are obtained with the enzyme in semi-purified form.

Depilation has hitherto been accomplished via numerous well-known methods, of which the most commonly used consists of treating the skins with alkaline reducing baths or pastes, particularly those containing lime and sodium sulphide. This process of depilation does not cause the removal of the hair by destroying its bonds to the skin, but instead causes a dissolution of the hair in the treatment bath, which must be renewed after each operation. It is therefore necessary to dispose of water which is very heavily charged with sulphide and organic products, of which the chemical oxygen demand and biological oxygen demand (COD and BOD) are extremely high. Disposal thus creates water pollution problems. Although it is possible to reduce the BOD and COD in waste streams by modern water purification equipment, their installation and operating costs are extremely high and make such a solution economically infeasible. One of the greatest advantages of the present invention is that it reduces by about half the pollution due to conventional depilation. In fact, the depilation of skins by means of enzymes which attack the part of the epidermis which bonds the hair to the skin makes it possible to recover the detached hair by simple filtration of the depilation bath, without causing water pollution.

Another advantage of the process according to the invention is that, as opposed to the conventional processes of enzymatic depilation, it is possible to recover the skin intact, without deterioration of the leather. In fact, as currently practiced, enzymatic depilation causes substantial degradation of the epidermis and even some of the dermis of the treated skins, resulting in leathers of very poor quality. This is primarily due to the fact that before now those skilled in the art have not had an enzyme available which acts specifically on the hair-skin bond. As heretofore practiced, the conventional enzymes react equally with the proteins of the deep layers of the skin as well as the hair so that the resulting leather exhibits a veining and spongy, damaged surface.

The advantage accorded by the present invention is particularly valuable in the case of depilation of sheepskins because, contrary to the conventional process of depilation by heating the sheepskins, depilation with the enzyme of the present invention makes it possible to obtain intact wool and an intact skin.

According to one embodiment of the present invention, cattle skins are depilated by contacting the skins with the enzyme 24,199 RP in a depilation vessel in which the percentage of water relative to the skin is between about 10 and 45% by volume and preferably between about 20 and 25%. The operation lasts about 3 to 24 hours. The temperature of the bath is preferably between about 24° and 30° C., while the pH of the bath corresponds to the maximum proteolytic activity of the enzyme, that is to say is between about 7 and 8.5. The pH must be kept constant during the operation by using a buffer solution which usually is prepared by adding trisodium phosphate or borax to the depilation vessel. Preferably, the enzyme is added such that from 0.3 to 1 parts by weight of enzyme 24,199 RP per 100 parts by weight of skins are present in the vessel.

In practice, the treatment of the skins is normally accomplished by either immersion in a solution containing between about 10 and 30 g/l of enzyme 24,199 RP (the strength of the enzyme being about 290 KU/g) or by applying via a spray gun a solution containing between about 1 and 10 g/liter of enzyme 24,199 RP (the strength of which is about 290 KU/g) when sheepskins are being treated.

The depilation vessel can be any trough or drum such as those used in the techniques known to those of skill in the art. It is advantageously fitted with an intermittent agitation device which improves the distribution of reagents over the skins. Agitation speeds in the order of ¾ revolution per minute have given particularly satisfactory results.

To insure that the removal of hair from the skin will be complete, the action of the enzyme is preferably followed by mechanical stripping of the skin by any suitable means. This mechanical stripping can be, quite simply, the friction of the skins against one another during the normal course of the process, optionally augmented by a brief period of more intense agitation. It can also consist of passing the skins treated by the process according to the invention through an unhairing machine which produces intact and non-felted skins.

According to another embodiment, the process of the present invention is preceded and/or followed by a large number of associated operations. For example, cleaning of the skins before depilation is often desirable. Cleaning can be accomplished by washing with water in a drum or on a paddle and is primarily intended to free the skin from impregnated salt used as a preservative. Washing can be followed by degreasing with the aid of conventional aromatic or chlorinated solvents or detergents in aqueous solution. This operation results in the removal of a large number of organic impurities, such as greases and minerals which soil the skin and obstruct the hair follicles. The degreasing is advantageously followed by a fresh water wash to obtain a skin which is as clean as possible and free from impurities and cleaning agents.

After these preliminary operations, it is often useful to carry out a pretanning operation which reinforces the dermis against the harmful action of the enzymes. However, such a pretanning operation must be very slight to avoid fixing the skin. In such operations, monoaldehydes or dialdehydes, such as formaldehyde are particularly useful.

Following depilation of the skins, they are washed and drained. The wash waters contain the intact skins and the enzyme, which can be separated by known means, such as decanting or filtration. The skins are then normally introduced into a pit of pure lime where they are hydrolyzed. This pit can be re-used often because the skins are very clean and only soil the pit slightly. After treatment in the pit, the hair side of the skins is undamaged and adheres perfectly to the dermis. Conversely, a skin depilated by means of free enzymes exhibits a deteriorated hair side, which is gelatinous to the touch and is in some areas detached from the dermis which is itself attacked.

In the course of the actual depilation operation, according to the invention, the discharge of polluting products is reduced considerably. This is particularly noticeable in the case of sulphides and dissolved skins. No trace is found in the wash waters resulting from the process of the invention whereas, they are copious in the residues resulting from processes of depilation by dissolving the skin. Furthermore, the enzyme, which is readily recovered by filtration, is not discharged with the effluents.

After treatment of the skins according to the process of the invention, all the conventional tanning operations as for example bating, pickling, chrome tanning, shaving and skiving, retanning, nourishing, drying, staking and finishing, can be performed. The leathers thus obtained exhibit a very fine grain, of a quality superior to that produced by the lime-sulphide method, an absence of veins and very good adhesion of the hair side, even on pieces taken from animal sides.

A comparative table of the results obtained for the depilation of cattle skins in accordance with the following three processes of depilation is given in Table VII:

(A) Process according to the invention: use of enzyme 24,199 RP according to Example 4, infra.
(B) Process using free enzymes.
(C) Process involving dissolving the skin in a bath containing lime and sodium sulphide.

TABLE VII

|  | C<br>Depilation<br>by lime-<br>sulphide | A<br>Process according to the<br>invention<br>Enzyme 24,199 RP | B<br>Depilation<br>by free<br>enzyme |
|---|---|---|---|
| Appearance of the hair side: |  |  |  |
| hair follicles | marked | very marked | only slightly marked |
| surface | flat | full | very flat |
| Touch | supple | slightly firm | slightly firm |
| Flexibiity | good | good | good |
| Filling of flaws in the flanks | slight | good | medium |
| Adhesion of the hair side | poor in the flanks | very good overall | poor in the flanks |
| Tensile strength in $kg/mm^2$ | 1.4 | 1.5 | 1.5 |
| Elongation at break in % | 59 | 65 | 66 |
| Sag which causes cracking, in mm | 7.2 | 7.4 | 7.5 |

The sag which causes cracking, measured on a Lastometer, demonstrates the ability of a leather to undergo folding under tension.

The examples which follow and are provided to further illustrate the various embodiments of the invention and are in no way intended to limit the scope of the invention. The activity of the products is expressed in Kunitz units (K.U.), defined above. This activity is expressed in K.U./cm³ where a product in solution is involved and in K.U./g where a solid product is involved.

EXAMPLE 1

Fermentation

A 170 liter fermenter was charged with the following:

| Peptone | 1,200 g. |
|---|---|
| yeast extract | 600 g. |
| agar | 240 g. |
| water, q.s.p. | 105 liters |

The pH of the medium was 6.55. It was sterilized by bubbling steam at 122° C. through it for 40 minutes. After cooling, because of the condensation of the steam during sterilization, the volume of the broth was 115 liters; it was raised to 120 liters by addition of 5 liters of a sterile aqueous solution containing:

| Glucose monohydrate | 1,200 g. |
|---|---|

The pH of the medium was 6.80. It was inoculated with a culture (200 cc.), prepared in an agitated Erlenmeyer flask, of *Streptomyces caligosus* DS 14,486. The culture was developed at 27° C. for 23 hours while agitating the aerating with sterile air. It was then suitable for the inoculation of the production culture.

The production culture was carried out in an 800 liter fermenter charged with the following substances:

| distiller's solubles | 16 kg. |
|---|---|
| sucrose | 6 kg. |
| soya oil | 4 liters |
| manganese sulphate | 0.08 kg. |
| water | 370 liters |

The pH was adjusted to 7.30 by addition of 10 N sodium hydroxide solution (850 cc.) and the medium was then sterilized by bubbling steam at 122° C. through it for 40 minutes. After cooling, because of the condensation of the steam during sterilization, the volume of the broth was 400 liters. The pH was 6.60.

It was then inoculated with the inoculum culture (40 liters), produced in the 170 liter fermenter, described above. The culture was developed at 27° C. for 94 hours while agitating by means of a turbine revolving at 205 revolutions/minute and aerating with a volume of sterile air of 20 m³/hr. The pH of the culture was at that stage 7.30 and the volume of the must was 400 liters. The proteolytic activity of the must at pH 7 and at 37° C. was 3.7 KU/cm³.

EXAMPLE 2

Extraction

The must (11 liters) obtained as in Example 1 was filtered and the filter cake was washed with 4 liters of distilled water. The filtrate and the wash liquors were combined and concentrated to 2 liters under reduced pressure (5 mm Hg) without exceeding 30° C. Acetone (2.4 liters) previously cooled to $-10°$ C. was added rapidly to the concentrate which had been cooled to $+4°$ C., while stirring. Stirring was continued for 2 minutes and the insoluble matter formed was separated by centrifuging at $+4°$ C. and at 5,000 g for 10 minutes. The insoluble matter obtained was extracted with water (450 cc. followed by 150 cc.) at $+4°$ C. for 2 hours, each time separating the insoluble matter by centrifuging at $+4°$ C. and at 5,000 g for 10 minutes. An aqueous extract (a total of 800 cc.) was obtained, the pH of which was between 7 and 7.5.

This extract was maintained at $+4°$ C. and crystalline ammonium sulphate (344 g.) was added while stirring. Stirring was continued for 15 minutes after the addition, the mixture was left to stand for one hour, and the active insoluble matter was then isolated by centrifuging at 10,000 g for 10 minutes at $+4°$ C. The insoluble matter was dissolved by stirring for one hour in water (500 cc.) while the pH was adjusted to about 7-7.5. The resulting solution was dialyzed at $+4°$ C. for 17 hours against distilled water.

A dialyzed extract (920 cc.) was obtained, into which acetone (1.1 liters) cooled to $-10°$ C. was poured rapidly, while stirring. The insolubilized enzyme was separated by centrifuging at 5,000 g for 10 minutes at $+4°$ C., and was subsequently dried under reduced pressure at $+4°$ C. in the presence of a dehydrating agent ($P_2O_5$).

Finally, enzyme 24,199 RP (9.5 g.), having the following enzymatic activities, was obtained.

| protease activity | 1,470 KU/g. |
|---|---|
| coagulant activity | 14,500 PU/g. |
| fibrinolytic activity | 4,920 LU/g. |

EXAMPLE 3

The must (360 l.) obtained in Example 1 was filtered on a filterpress in the presence of a filtration adjuvant (25 kg.). Methanol (400 liters) cooled to $-10°$ C. was added to the filtrate (200 liters) obtained. After cooling the mixture to about $-10°$ C., the resulting precipitate was separated by centrifuging cold, and was dried under reduced pressure at 35° C.

Crude 24,199 RP (229 g.) containing 290 KU/g. was thus isolated.

EXAMPLE 4

Application to the Depilation of Cattle Skins

Green-cured cattle skins (100 kg.) were first desalted twice by agitating for 30 minutes in pure water (200%) (the percentage are expressed relative to the weight of the cured skins) and then soaked.

The desalted skins were agitated slowly for 20 hours at a temperature of between 20° and 25° C. in water (200%) to which sodium hydroxide flakes (0.2%) and alkaline protease S 1,200 (0.05%) had been added. The skins were then fleshed after which the depilation was performed.

The fleshed skins were placed in a drum turning at a speed of 3 to 4 revolutions per minute for 1 hour. Water (20 to 25%) and enzyme 24,199 RP (300 to 400 g.) containing 290 KU/g. were added. The temperature inside the drum was adjusted to 30° C. The skins were agitated as described above for 1 hour and then intermittently for 8 to 9 hours. The hair could at that stage be removed perfectly by rubbing with the back of a blade. The skins were then unhaired by means conventional to the tanning industry.

The pelt thus obtained was virtually, completely depilated except for a few very short tufts which had escaped the mechanical working with the blade.

The skins were then treated in a known manner in a liming liquor (200%) made with lime (3%) and sodium sulphide (1.5%). The object of this treatment was to obtain perfectly dipilated skins which could be subjected to the subsequent operations of the tanning process.

The liming liquor, which was only very slightly loaded, could be recycled. The skins obtained after tanning, dressing and finishing had an attractive appearance, and a fine hairside which was undamaged and glossy and adhered very firmly, contrary to the skins ordinarily treated with proteases.

EXAMPLE 5

Application to the Dewoolling of Sheepskins

After soaking sheepskins, removing fatty matter from the flesh side and draining, an aqueous solution (150 cc.) containing enzyme 24,199 RP (5 to 6 g/liter), of strength 290 KU/g. and the solution, buffered to pH 8.5 with disodium phosphate, was applied by a spray gun to the flesh side of each skin. The skins were stacked flesh side against flesh side in a chamber where the relative humidity did not exceed 85% and where the temperature was kept at between about 24° and 26° C. After 16 to 20 hours, dewoolling could be carried out very easily by the usual means.

The wool obtained was of very good quality, as was the skin which remained, which had not lost its outer face, contrary to the skins obtained by the "heating" process. The skin was subsequently limed, after which it was tanned and finished in accordance with the usual processes.

While the invention has now been described in terms of various preferred embodiments, the skilled artisan will readily appreciate that various substitutions, modifications, changes, and omissions, may be made without departing from the spirit thereof. Accordingly, it is intended that the scope of the present invention be limited solely by that of the following claims.

What is claimed is:

1. A biologically pure culture of the microorganism *Strepomyces caligosus* DS 14,486, having the identifying characteristics of NRRL 8,195, said culture being capable of producing the proteolytic enzyme, 24,199 RP, in a recoverable quantity upon culturing in a nutrient medium comprising assimilable sources of carbon and nitrogen and inorganic constituents.

2. A process for preparing the proteolytic enzyme, 24,199 RP, which comprises culturing *Streptomyces caligosus* DS 14,486, having the identifying characteristics of NRRL 8,195, in a nutrient medium containing sources of assimilable carbon and nitrogen and inorganic constituents under aerobic conditions and removing the enzyme formed from said culture.

3. The process as defined by claim 2, wherein said source of assimilable carbon comprises at least one compound selected from the group consisting of carbohydrates, sugar alcohols, organic acids, animal oils and vegetable oils.

4. The process as defined by claim 2, wherein said source of assimilable nitrogen comprises at least one compound selected from the group consisting of inorganic and organic ammonium salts, urea, aminoacids, and compounds which contain nitrogen in protein form.

5. The process as defined by claim 2, wherein said inorganic constituents comprise at least one compound selected from the group consisting of alkali metal and alkaline earth metal phosphates, calcium and magnesium carbonate, alkali metal and alkaline earth metal chlorides and sulphates and salts of zinc, cobalt, iron, copper and manganese.

6. The process as defined by claim 2, wherein said nutrient medium contains growth factors selected from the group consisting of riboflavin, folic acid, and pantothenic acid.

7. A proteolytic enzyme produced by culturing *Streptomyces caligosus* DS 14,486, said enzyme comprising a protein substance in the form of a powder having a brown to black color, a molecular weight of about 27,000, and an isoelectric point of about 3.7, said enzyme being rather soluble in water, slightly soluble in concentrated aqueous solutions of neutral salts and in water-alcohol or water-acetone mixtures and virtually insoluble in anhydrous alcohols and ketones and having a maximum activity on casein at a pH of 7.5 and a temperature of 45° C., a coagulant activity on milk and a fibrinolytic activity on a fibrin clot and having a specific activity on the hair-skin bond such that in use in a process for the enzymatic depilation of animal skin, said enzyme affords recovery of both intact hair and intact skin.

8. A process for the enzymatic depilation of animal skins comprising contacting the skins with a proteolytic enzyme produced by culturing *Streptomyces caligosus* DS 14,486, said enzyme comprising a protein substance in the form of a powder having a brown to black color, a molecular weight of about 27,000, and an isoelectric point of about 3.7, said enzyme being rather soluble in water, slightly soluble in concentrated aqueous solutions of neutral salts and in water-alcohol or water-acetone mixtures and virtually insoluble in anhydrous alcohols and ketones and having a maximum activity on casein at a pH of 7.5 and a temperature of 45° C., a coagulant activity on milk and a fibrinolytic activity on a fibrin clot and having a specific activity on the hair-skin bond such that in use in a process for the enzymatic depilation of animal skin, said enzyme affords recovery of both intact hair and intact skin.

9. The process as defined by claim 8, wherein said animal skins are cattle skins and where said skins and said proteolytic enzyme are contacted in a depilation vessel containing between about 10 to 45% water by volume relative to the skins for between about 3 to 24 hours, and thereafter treating said skins in a liming liquor.

10. The process as defined by claim 9, wherein the amount of enzyme admitted to the depilation vessel is such that about 0.3 to 1 part by weight enzyme is employed per 100 parts by weight skins.

11. The process as defined by claim 10, wherein the temperature of the depilation solution is from about 24° to 30° C. and its pH is between about 7 and 8.5.

12. The process as defined by claim 8, wherein said animal skins are sheepskins and said skins and said proteolytic enzyme are contacted by spraying the enzyme in an aqueous solution on the flesh side of the skin and thereafter stacking the skins flesh side against flesh side in a chamber in which the relative humidity does not exceed about 85% and the temperature is between about 24° and 26° C. for a period of about 16 to 20 hours.

13. The process as defined by claim 12, wherein the percentage of water relative to said skins in said depilation vessel is between about 10 and 45% by volume relative to said skins.

14. The proteolytic enzyme 24,199 RP prepared by the process of claim 2, said enzyme comprising a protein substance in the form of a powder having a brown to black color, a molecular weight of about 27,000, and an isoelectric point of about 3.7, said enzyme being rather soluble in water, slightly soluble in concentrated aqueous solutions of neutral salts and in water-alcohol or water-acetone mixtures and virtually insoluble in anhydrous alcohols and ketones and having a maximum activity on casein at a pH of 7.5 and a temperature of 45° C., a coagulant activity on milk and a fibrinolytic activity on a fibrin clot and having a specific activity on the hair-skin bond such that in use in a process for the enzymatic depilation of animal skin, said enzyme affords recovery of both intact hair and intact skin.

* * * * *